(12) United States Patent  
Ramakrishnan et al.

(10) Patent No.: US 8,774,933 B2
(45) Date of Patent: *Jul. 8, 2014

(54) POWER EFFICIENCY IN A MEDICAL IMPLANT BASED SYSTEM

(71) Applicant: Texas Instruments Incorporated, Dallas, TX (US)

(72) Inventors: Sthanunathan Ramakrishnan, Bangalore (IN); Jaiganesh Balakrishnan, Bangalore (IN)

(73) Assignee: Texas Instruments Incorporated, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/019,113

(22) Filed: Sep. 5, 2013

(65) Prior Publication Data

US 2014/0005751 A1    Jan. 2, 2014

Related U.S. Application Data

(62) Division of application No. 12/536,592, filed on Aug. 6, 2009, now Pat. No. 8,554,334.

(60) Provisional application No. 61/088,074, filed on Aug. 12, 2008, provisional application No. 61/086,663, filed on Aug. 6, 2008.

(51) Int. Cl.
  *A61N 1/18* (2006.01)

(52) U.S. Cl.
  USPC .................................................. 607/60

(58) Field of Classification Search
  USPC ............................. 607/32–33, 59–60
  See application file for complete search history.

(56) References Cited

U.S. PATENT DOCUMENTS

| | | | |
|---|---|---|---|
| 7,110,823 B2 | 9/2006 | Whitehurst et al. | |
| 8,554,334 B2 * | 10/2013 | Ramakrishnan et al. | 607/60 |
| 2009/0105567 A1 | 4/2009 | Smith et al. | |

\* cited by examiner

*Primary Examiner* — Amanda Patton
(74) *Attorney, Agent, or Firm* — Michael A. Davis, Jr.; Frederick J. Telecky, Jr.

(57) ABSTRACT

By a medical implant transceiver implantable within a body of a living organism, a portion of a signal is received from a medical controller transceiver external to the body of the living organism. Based on directions within the portion of the signal, a time duration is determined, after which a subsequent portion of the signal is to be transmitted from the medical controller transceiver. The directions include a value indicative of the time duration. The time duration differs based on the value. The subsequent portion is to be transmitted from the medical controller transceiver after an end of the portion. The medical implant transceiver enters into an inactive state for the time duration and awakens after the time duration has elapsed.

15 Claims, 3 Drawing Sheets

2

POWER EFFICIENCY IN A MEDICAL IMPLANT BASED SYSTEM

CROSS-REFERENCE TO RELATED APPLICATIONS

This application is a divisional of U.S. patent application Ser. No. 12/536,592, filed Aug. 6, 2009, entitled POWER OPTMIZATION IN A MEDICAL IMPLANT BASED SYSTEM, naming Sthanunathan Ramakrishnan et al. as inventors, which is hereby fully incorporated herein by reference for all purposes, and which claims priority from U.S. Provisional Application Ser. No. 61/086,663, filed Aug. 6, 2008, entitled WAKE-UP SIGNALING IN MICS IMPLANTS and from U.S. Provisional Application Ser. No. 61/088,074, filed Aug. 12, 2008, entitled PACKET STRUCTURE AND TRANSMISSION STRATEGY FOR OPTIMIZING POWER CONSUMPTION IN MEDICAL IMPLANTS, which are incorporated therein and herein by reference in their entirety.

BACKGROUND

The disclosures herein relate in general to medical implant based systems, and in particular to power efficiency in a medical implant based system.

A medical implant based system includes a medical controller and a medical implant. The medical implant is present inside the body of a living organism and the medical controller is external. Power consumption of the medical implant is one of the major determinants of lifetime of the medical implant. The power consumption in a medical implant transceiver forms a significant portion of the overall power consumption in the medical implant. Hence, it is desired to improve efficiency of power consumption in the medical implant transceiver to increase lifetime of the medical implant.

The power in the medical implant transceiver is utilized for performing various functions. In one example, power consumption in the medical implant transceiver is dominated by a listen mode of the medical implant transceiver. In the listen mode, the medical implant transceiver wakes up periodically, for example every 4 seconds, and searches for a signal for association. The signal for association can be transmitted for a time period greater than 4 seconds. The medical implant transceiver that wakes up at beginning of transmission of the signal for association has to wait till end of the transmission of the signal for association to perform further functions. The waiting leads to power wastage.

In another example, the medical implant transceiver searches for a poll signal when the medical implant transceiver is associated with the medical controller transceiver. In one scenario, there might be a time uncertainty between the medical implant transceiver and the medical controller transceiver which may cause the medical implant transceiver to listen to an undesired transmission, and in turn result in loss of session with the medical controller transceiver and de-association. The listen mode is then activated. Power consumed in the listen mode is higher as compared to power consumed, by the medical implant transceiver, when the poll signal is detected. In another scenario, the medical implant transceiver may not be de-associated and may not be in close proximity to the medical controller transceiver. The medical implant transceiver searches for the poll signal, based on the time uncertainty, before deciding that the poll signal is not present, which leads to power wastage. The medical implant transceiver performs the search multiple times before de-associating with the medical controller transceiver which results in power wastage. The situation worsens when the time uncertainty is large.

SUMMARY

By a medical implant transceiver implantable within a body of a living organism, a portion of a signal is received from a medical controller transceiver external to the body of the living organism. Based on directions within the portion of the signal, a time duration is determined, after which a subsequent portion of the signal is to be transmitted from the medical controller transceiver. The directions include a value indicative of the time duration. The time duration differs based on the value. The subsequent portion is to be transmitted from the medical controller transceiver after an end of the portion. The medical implant transceiver enters into an inactive state for the time duration and awakens after the time duration has elapsed.

BRIEF DESCRIPTION OF THE VIEWS OF DRAWINGS

In the accompanying figures, similar reference numerals may refer to identical or functionally similar elements. These reference numerals are used in the detailed description to illustrate various embodiments and to explain various aspects and advantages of the disclosure.

DETAILED DESCRIPTION OF THE EMBODIMENTS

Figure 1:
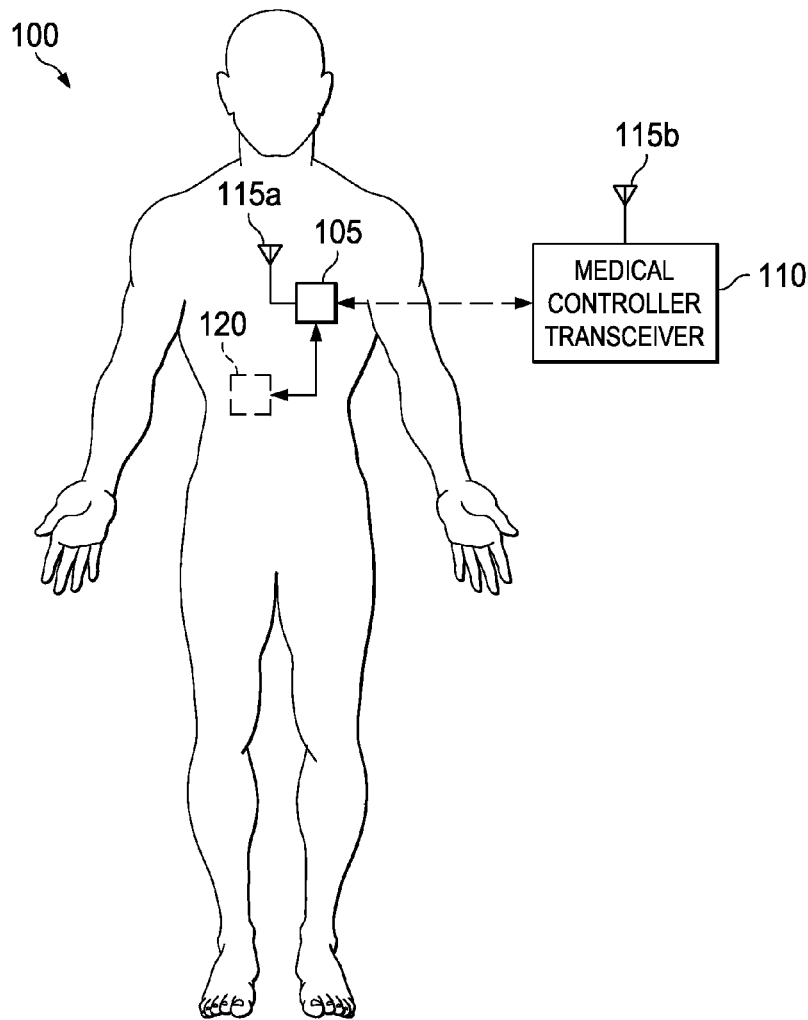
FIG. 1 illustrates an environment, in accordance with one embodiment.

FIG. 1 illustrates an environment 100 including a medical implant based system. The environment 100 includes one or more medical implant transceivers, for example a medical implant transceiver 105, hereinafter referred to as the implant transceiver 105, and one or more medical controller transceivers, for example a medical controller transceiver 110, hereinafter referred to as the controller transceiver 110. The implant transceiver 105 is present inside a living organism to monitor health and to transmit health details to the controller transceiver 110. The implant transceiver 105 is included in a medical implant. The controller transceiver 110 is included in a medical controller.

The implant transceiver 105 includes or is connected to an antenna 115a to transmit and receive signals. The implant transceiver 105 can also include or be connected to sensors, for example a sensor 120. Each sensor monitors and senses various health details. Examples of the sensors include, but are not limited to, pacemakers and brain sensors. The controller transceiver 110 also includes or is connected to an antenna 115b to transmit and receive signals.

The implant transceiver 105, and the controller transceiver 110, can communicate with each other in a Medical Implant Communication Service (MICS) frequency band. The MICS frequency band ranges from 402 megahertz (MHz) to 405 MHz. The implant transceiver 105 and the controller transceiver 110 can also communicate with each other in a Medical Data Services (MEDS) frequency band. The MEDS frequency band ranges from 401 MHz to 402 MHz, and from 405 MHz to 406 MHz. The frequency band can be referred to as a band of channels.

A communication session is initiated by the controller transceiver 110. The controller transceiver 110 selects a channel for transmission based on certain parameters. In one example, the controller transceiver 110 selects either a least interfered channel or a channel which has interference power below a threshold. The selection process can be referred to as "Listen Before Talk" (LBT). The controller transceiver 110 then transmits a signal in the channel. The signal can be of various types, for example a signal for association, a poll signal and a signal for data transfer.

The implant transceiver 105 can have two states, an associated state and an unassociated state (listen mode). The associated state can be defined as a state in which the implant transceiver 105 is associated with the controller transceiver 110. The unassociated state can be defined as a state in which the implant transceiver 105 is not associated with the controller transceiver 110. The medical implant transceiver 105 transitions between an active state and an inactive state (a sleep state) irrespective of being in the associated state or the unassociated state. In the unassociated state, the duration of sleep and the time at which the implant goes to sleep are determined unilaterally by the implant while in the associated state, the duration of sleep and the time are determined by the implant based on directions from the controller. The implant transceiver 105 spends bulk of the time in the inactive state. In the active state, the implant transceiver 105 receives, transmits and processes signals which lead to power consumption.

Figure 2A:
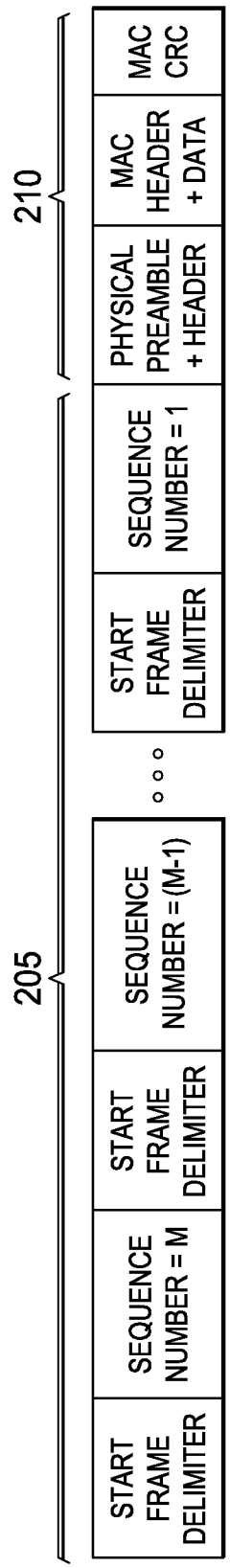
FIG. 2A illustrates an exemplary structure of a signal, in accordance with one embodiment.
Figure 2B:
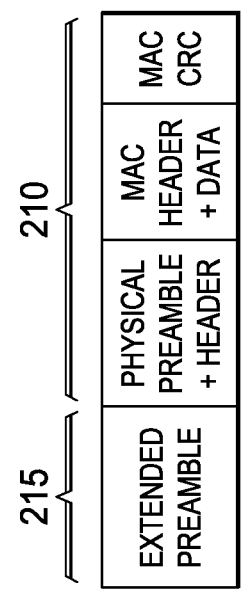
FIG. 2B illustrates an exemplary structure of a signal, in accordance with another embodiment.

An exemplary structure of a signal transmitted by the controller transceiver 110 for power efficiency is explained in detail in conjunction with FIGS. 2A and 2B.

FIG. 2A illustrates an exemplary structure of a signal. The signal includes various portions or packets. The portions can include a portion 205 and a subsequent portion 210. The subsequent portion 210 follows the portion 205 and is transmitted at end of the portion. The signal can also have other portions. Each portion can be processed at a different layer. Examples of layers, in order from lower layer to higher layer, include a physical layer, a medium access control (MAC) layer and other higher layers. A controller transceiver encodes the signal by processing portions at various layers. The controller transceiver starts encoding the portions at a highest layer and adds data corresponding to each layer as the portions move from the highest layer towards the physical layer. At an implant transceiver, when functioning as a receiver, the portions move from the physical layer towards the higher layers. The implant transceiver starts decoding the portions at the physical layer and removes data corresponding to each layer as the portions move from the physical layer towards the higher layers.

The portion 205 includes sequence numbers and multiple instances of a SFD. The SFD indicates location of a sequence number. The SFD can be an 18 bit value or 2 bytes value. A particular bit pattern can be set as the SFD. The SFD is followed by a sequence number field which is indicative of a time duration after which the subsequent portion 210 of the signal will start. The sequence number can be a 16 bit or a 14 bit value. The implant transceiver detects the SFD and determines following bits as the sequence number. The sequence numbers proceed in a sequential order, for example a decrementing order M to 1. The time duration after which the subsequent portion 210 will start can be determined from a Kth sequence number as K*(time occupied by one SFD+one sequence number). The sequence numbers can also be arranged in an incrementing order from L to $2^N-1$, where $2^N-L$ is the number of times the SFD and sequence number field is repeated. Each sequence number is preceded by the SFD. None of the sequence numbers match the SFD. For example, if the SFD is a pattern of scrambled zeros the sequence number decrements till 1 and not zero. The time spent by the implant transceiver in decoding is also less as the implant transceiver needs to decode the SFD and the sequence number. The implant transceiver remains in the sleep state until the end of the portion 205 and wakes up at the beginning of the subsequent portion 210.

The portion 205 and the subsequent portion 210 can be referred to as a beacon. The portion 205 can be referred to as a preamble for the subsequent portion 210.

The subsequent portion 210 can be referred to as a physical layer portion. The subsequent portion 210 can include a preamble and a header field for a physical layer, a medium access control (MAC) header, data field, and a MAC cyclic redundancy check (CRC) field. The subsequent portion 210 can also include other information needed by the implant transceiver when the implant transceiver wakes up to receive the subsequent portion 210.

The header field for the physical layer can include information associated with the controller transceiver and the implant transceiver. The MAC header includes MAC identifications which can be used to verify whether the signal is intended for the implant transceiver or not. The data field includes information regarding data transmission. A MAC Cyclic Redundancy Check (CRC) field performs CRC computations using MAC header bits. The CRC computations provide protection against unexpected errors. The subsequent portion 210 can be processed by removing the header filed and the preamble for the physical layer, and sending the subsequent portion 210 to a MAC layer for processing.

The portion 205 and the subsequent portion 210 can be included in a signal for association or a poll signal. The portion 205 enables the implant transceiver to determine the time duration after which the subsequent portion 210 will be transmitted.

In one embodiment, the portion 205 can be transmitted for a period greater than sleep time of the implant transceiver. In another embodiment, the portion 205 can be transmitted at different time durations. For example, if total time covered by one cycle of the implant transceiver is 5 seconds in which the implant transceiver is in active state for 0.5 seconds and is in sleep state for 4.5 seconds then the different time durations can include 1 to 2 seconds in a first cycle, 2 to 3 seconds in a second time cycle and so on.

In some embodiments, the signal structure can include the SFD, followed by a sequence number, followed by a part of the subsequent portion 210, followed by the SFD, followed by a subsequent sequence number and so on.

When the implant transceiver is associated with the controller transceiver, a time uncertainty can exist between the implant transceiver and the controller transceiver. The time uncertainty can be defined as a mismatch between the time at which the controller transceiver intends to send the data and the time at which the implant transceiver, associated with the controller transceiver, is expecting the data. The controller transceiver determines structure of the poll signal based on the time uncertainty of the implant transceiver. If the time uncertainty exceeds a threshold then the signal including the portion 205 and the subsequent portion 210 is selected. The portion 205 can be modified by including sequence numbers based on the time uncertainty. In one example, the portion 205 can be modified by including sequence numbers and multiple instances of SFD for a time equivalent to twice the time uncertainty. If the time uncertainty does not exceed the threshold then the controller transceiver can modify the subsequent portion 210 by extending preamble in the subsequent portion 210. An exemplary signal structure with modified subsequent portion is shown in FIG. 2B.

Referring to FIG. 2B, the subsequent portion 210 is extended by adding a portion 215. The portion 215 can be generated by extending the preamble of the physical layer. The portion 215 can be twice the time uncertainty. On completion of the portion 215, the subsequent portion 210 follows. The subsequent portion 210 is sent in the same channel as the portion 205 and the portion 215. This enables the medical implant transceiver to wake up and receive the subsequent portion 210, and need not scan the band of channels. Also, if the implant transceiver is not in close proximity to the controller transceiver and is not de-associated, the implant transceiver spends minimal time in searching for signals. For example, when a living organism including the implant transceiver travels out of home to work or if the living organism travels away from the controller transceiver at home, the implant transceiver searches for the signal for the minimal time and decides that the signal is not present.

The modification of the portion 205 or the subsequent portion 210 also prevents the implant transceiver from listening to interferences or noise or any other signals not intended for the implant transceiver, and saves power.

Figure 3:
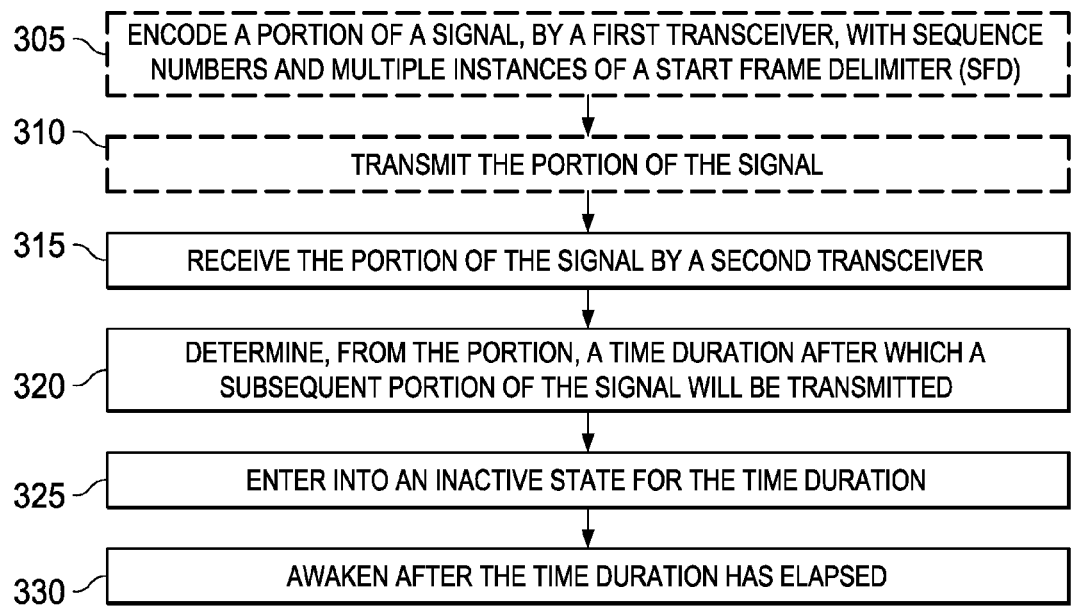
FIG. 3 illustrates a method for power efficiency, in accordance with one embodiment.

FIG. 3 illustrates a method for power efficiency. In some embodiments, step 305 and step 310 are performed by a second transceiver, for example a controller transceiver, and step 315 to step 330 are performed by a first transceiver, for example an implant transceiver.

At step 305, a portion of a signal is encoded, for example with sequence numbers and multiple instances of a SFD, by the controller transceiver. The signal can be a signal for association or a poll signal. The portion can be encoded with decrementing sequence numbers or incrementing sequence numbers. Each sequence number is preceded by the SFD. The SFD is dissimilar to each sequence number. The portion of the signal is then transmitted at step 310. The portion of the signal for association can be transmitted for a period greater than sleep time of the second transceiver, for example the implant transceiver. For example, if the sleep time is 4 seconds, then the controller transceiver can transmit the signal for a period greater than 4 seconds.

When the implant transceiver is associated with the controller transceiver, the controller transceiver indicates the time for which the implant transceiver should be in inactive state before waking up and transitioning to an active state. In the active state, the implant transceiver expects the poll signal from the transceiver before a session is established and data transfer is done. The period of inactive state can be high for the implant transceiver in the associated state as compared to that in the unassociated state. A time uncertainty can exist between the controller transceiver and the implant transceiver. The time uncertainty may either be known to the controller transceiver or can be transmitted by the implant transceiver to the controller transceiver during association or any other point of time.

For example, if the time uncertainty of the implant transceiver is +/−100 parts per million (ppm) and that of the controller transceiver is +/−100 ppm, then in a worst case, the time uncertainty between the implant transceiver and the controller transceiver can be +/−200 ppm. A transmission time can then be varied based on the +/−200 ppm. For example, if the sleep time of the implant transceiver is 5 minutes then the controller transceiver can determine the time uncertainty as +/−60 milliseconds [5*60*200*10^(−6)]. The controller transceiver then modifies the poll signal based on the time uncertainty. The time uncertainty is checked against a threshold. If the time uncertainty exceeds the threshold then the portion of the signal can be modified by inserting changing sequence numbers and multiple instances of the SFD. In one example, the time duration of the changing sequence numbers and the multiple instances of the SFD is equivalent to twice the time uncertainty, for example 120 milliseconds. If the time uncertainty does not exceed the threshold, then the controller transceiver can modify a subsequent portion of the signal by extending the preamble for the time equivalent to twice the time uncertainty. In one example, the threshold is 50 milliseconds. The controller transceiver then extends the preamble by 120 milliseconds and starts the transmission 60 milliseconds before designated sleep time of the implant expires. The controller transceiver modifies the transmission time based on the time uncertainty. In the illustrated example of 5 minutes sleep time, the controller transceiver starts transmission at 4.94 minutes (5 minutes-60 milliseconds) according to a clock of the controller transceiver. The modification in transmission time reduces listening time of the implant transceiver and hence saves power. The modification also protects the implant transceiver from listening to interferences.

At step 315, the portion of the signal is received by the implant transceiver. The implant transceiver receives the portion when the implant transceiver is in an active state. When the implant transceiver is in the unassociated state, then the implant transceiver receives the portion of the signal for association.

When the implant transceiver is in the associated state, the modifying ensures that the implant transceiver finds either modified portion of the poll signal or extension of the subsequent portion of the poll signal when the implant transceiver enters into the active state. The implant transceiver wakes up at a predefined time according to a clock of the implant transceiver to detect the signal. Detecting the signal includes either detecting the modified portion of the poll signal or extension of the subsequent portion of the poll signal. The modifying also prevents the implant transceiver from searching any channel other than a channel in which earlier communication was performed and locking onto any unwanted transmissions, for example the transmissions happening in an adjacent area or network.

At step 320, a time duration after which the subsequent portion of the signal will be transmitted is determined from the portion. The subsequent portion is transmitted at end of transmission of the portion. The SFD is detected in the portion of the signal for association or the modified portion of the poll signal. A sequence number succeeding the SFD is decoded and the time duration is determined.

At step 325, the implant transceiver enters into an inactive state for the time duration and saves power.

At step 330, the implant transceiver awakens after the time duration has elapsed to detect the subsequent portion which is transmitted at end of transmission of the portion. In some embodiments, the subsequent portion is transmitted in continuation to transmission of the portion and also in the same channel.

In some embodiments, if the implant transceiver finds the extension of the subsequent portion of the poll signal at step 315 then step 320 to step 330 can be bypassed and the implant transceiver continues to listen to the extension followed by the subsequent portion.

In one embodiment, when the implant transceiver is in the unassociated state then the implant transceiver can send an acknowledgement to the controller transceiver after receiving and processing the subsequent portion of the signal for association. In another embodiment, when the implant transceiver is in the associated state then the implant transceiver can perform data transfer with the controller transceiver after receiving and processing the subsequent portion of the poll signal.

Figure 4:
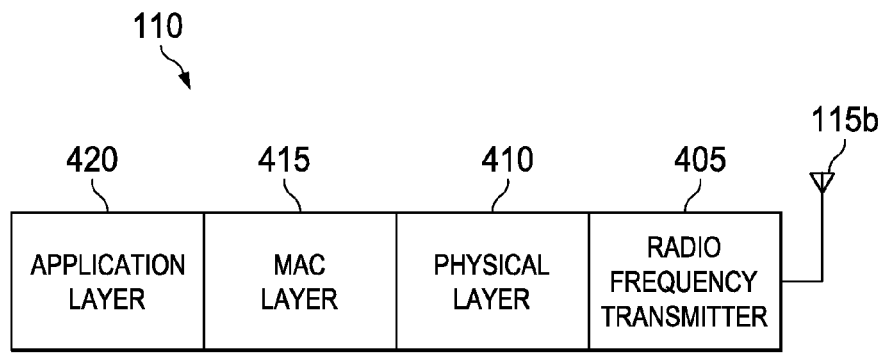
FIG. 4 illustrates a block diagram of a medical controller transceiver, in accordance with one embodiment.

FIG. 4 illustrates a block diagram of a portion of a controller transceiver, for example a controller transceiver 110. The controller transceiver 110 includes a radio frequency transmitter 405 that sends signals, for example a portion of a signal. The controller transceiver 110 includes several layers, for example a physical layer 410, a MAC layer 415, and an application layer 420 for processing the signal. An antenna 115b is connected to the radio frequency transmitter 405 to transmit signals.

The controller transceiver 110 also includes a radio frequency receiver that receives signals. In one embodiment, a radio frequency transceiver can be present for performing functions of the radio frequency transmitter 405 and the radio frequency receiver.

Each layer includes a circuit for performing specified functions. The circuit can operate in response to instructions stored in a memory or a machine-readable medium. Examples of the machine-readable medium include, but are not limited to, magnetic disks, optical disks and other electrical or magnetic storage medium.

A circuit of the physical layer 410 encodes the portion of the signal with sequence numbers and multiple instances of the SFD. The circuit places the SFD and sequence numbers at appropriate position of the signal and then modulates the bits onto a channel.

It is noted that various known circuits for the physical layer 410 can be used.

Figure 5:
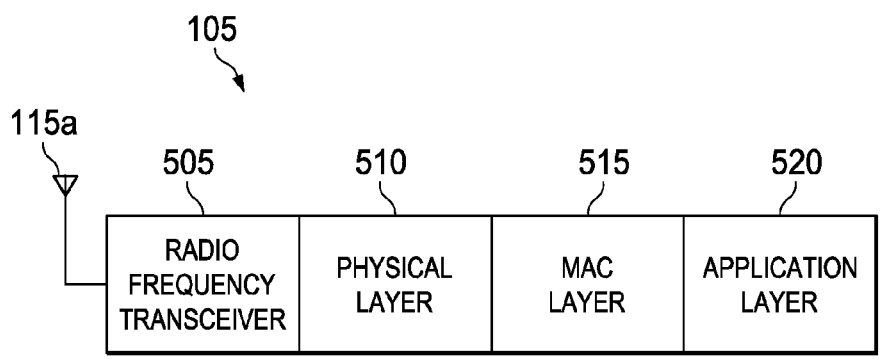
FIG. 5 illustrates a block diagram of a medical implant transceiver, in accordance with one embodiment.

FIG. 5 illustrates a block diagram of a portion of an implant transceiver, for example an implant transceiver 105. The implant transceiver 105 includes a radio frequency transceiver 505 that receives signals, for example a portion of a signal. The implant transceiver 105 includes several layers, for example a physical layer 510, a MAC layer 515, and an application layer 520, for processing the signal. An antenna 115a is connected to the radio frequency transceiver 505 to transmit and receive signals.

Each layer includes a circuit for performing specified functions. For example, a circuit of the physical layer 510 is responsive to the portion of the signal to detect a SFD in the portion of the signal and decodes a sequence number succeeding the SFD to determine a time duration after which a subsequent portion of the signal will be transmitted. The circuit of the physical layer 510 can include a decoder for decoding the sequence number. The circuit of the physical layer 510 further causes the implant transceiver 105 to enter into an inactive state for the time duration and to awaken after the time duration has elapsed. The logic for performing the functions can be hardcoded into the circuit.

It is noted that various known circuits for the physical layer 510 can be used.

Figure 6:
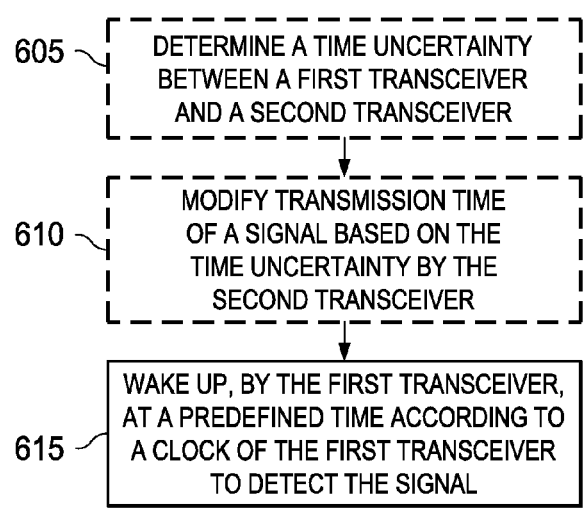
FIG. 6 illustrates a method for signaling in a medical implant based system, in accordance with one embodiment.

FIG. 6 illustrates a method for signaling. In some embodiments, step 605 and step 610 are performed by a second transceiver, for example a controller transceiver, and step 615 is performed by a first transceiver, for example an implant transceiver. At step 605, a time uncertainty between the implant transceiver and the controller transceiver is determined. The implant transceiver is associated with the controller transceiver. The controller transceiver also has information regarding time uncertainty of the implant transceiver. The information can be received by the controller transceiver in any of previous communications between the implant transceiver and the controller transceiver.

In some embodiments, step 605 can be bypassed and the controller transceiver can a priori have a predefined worst case time which can be referred to as the time uncertainty between the first transceiver and the second transceiver. At step 610, transmission time of the signal is modified by the controller transceiver based on the time uncertainty between the implant transceiver and the controller transceiver. Structure of the signal can also be modified. The structure can be modified by extending preamble if the time uncertainty does not exceed a threshold or by inserting sequence numbers and multiple instances of a SFD if the time uncertainty exceeds a threshold. The signal is then transmitted based on the modified time. At step 615, the implant transceiver wakes up, at a predefined time according to a clock of the first transceiver to detect the signal.

The foregoing description sets forth numerous specific details to convey a thorough understanding of embodiments of the disclosure. However, it will be apparent to one skilled in the art that embodiments of the disclosure may be practiced without these specific details. Some well-known features are not described in detail in order to avoid obscuring the disclosure. Other variations and embodiments are possible in light of above teachings, and it is thus intended that the scope of disclosure not be limited by this Detailed Description, but only by the Claims.

What is claimed is:

1. A method, comprising:
   by a medical implant transceiver implantable within a body of a living organism, receiving a portion of a signal from a medical controller transceiver external to the body of the living organism;
   based on directions within the portion of the signal, determining a time duration after which a subsequent portion of the signal is to be transmitted from the medical controller transceiver, wherein the directions include a value indicative of the time duration, wherein the time duration differs based on the value, and wherein the subsequent portion is to be transmitted from the medical controller transceiver after an end of the portion;
   causing the medical implant transceiver to enter into an inactive state for the time duration; and
   awakening the medical implant transceiver after the time duration has elapsed.

2. The method of claim 1, wherein determining the time duration includes:
   detecting a start frame delimiter (SFD) in the portion of the signal; and
   decoding a sequence number succeeding the SFD.

3. The method of claim 1, wherein awakening the medical implant transceiver includes:
   awakening the medical implant transceiver to detect the signal.

4. The method of claim 1, wherein awakening the medical implant transceiver includes:
   awakening the medical implant transceiver after the time duration has elapsed according to a clock of the medical implant transceiver.

5. The method of claim 1, and comprising:
   by the medical controller transceiver, transmitting the portion of the signal.

6. The method of claim 5, wherein transmitting the portion of the signal includes:
   transmitting the portion of the signal for a period greater than a sleep time of the medical implant transceiver.

7. The method of claim 5, and comprising:
   determining a time uncertainty between the medical implant transceiver and the medical controller transceiver.

8. The method of claim 7, and comprising:
   by the medical controller transceiver: in response to the time uncertainty exceeding a threshold, encoding the portion of the signal with at least first and second sequence numbers and multiple instances of a start frame delimiter (SFD), wherein each of the first and second sequence numbers is preceded by a respective instance of the SFD.

9. The method of claim 8, wherein the SFD is dissimilar to the at least first and second sequence numbers.

10. The method of claim 8, wherein encoding the portion of the signal includes one of:
   encoding the portion of the signal with decrementing sequence numbers; and
   encoding the portion of the signal with incrementing sequence numbers.

11. The method of claim 7, and comprising:
by the medical controller transceiver: in response to the time uncertainty being within a threshold, extending a preamble of the signal.

12. The method of claim 7, and comprising:
by the medical controller transceiver: modifying a transmission time of the signal based on the time uncertainty.

13. The method of claim 7, and comprising:
by the medical controller transceiver: modifying a structure of the signal based on the time uncertainty.

14. The method of claim 7, and comprising:
by the medical controller transceiver: modifying the portion of the signal based on the time uncertainty.

15. The method of claim 7, and comprising:
by the medical controller transceiver: modifying the subsequent portion of the signal based on the time uncertainty.

\* \* \* \* \*